United States Patent
Nishino et al.

(10) Patent No.: US 7,304,169 B2
(45) Date of Patent: Dec. 4, 2007

(54) PROCESS FOR PRODUCING TETRAHYDROPYRAN-4-OL, INTERMEDIATE THEREFOR, AND PROCESS FOR PRODUCING THE SAME

(75) Inventors: Shigeyoshi Nishino, Ube (JP); Kenji Hirotsu, Ube (JP); Hidetaka Shima, Ube (JP); Shinobu Suzuki, Ube (JP)

(73) Assignee: Ube Industries, Ltd., Ube-shi, Yamaguchi (JP)

(*) Notice: Subject to any disclaimer, the term of this patent is extended or adjusted under 35 U.S.C. 154(b) by 545 days.

(21) Appl. No.: 10/516,756

(22) PCT Filed: Jun. 10, 2003

(86) PCT No.: PCT/JP03/07357

§ 371 (c)(1),
(2), (4) Date: Dec. 3, 2004

(87) PCT Pub. No.: WO03/104215

PCT Pub. Date: Dec. 18, 2003

(65) Prior Publication Data

US 2005/0222439 A1      Oct. 6, 2005

(30) Foreign Application Priority Data

Jun. 10, 2002   (JP)  ............ 2002-168442

(51) Int. Cl.
*C07D 309/12*   (2006.01)
(52) U.S. Cl. ................. 549/420; 549/423
(58) Field of Classification Search ......... 549/420, 549/423
See application file for complete search history.

(56) References Cited

FOREIGN PATENT DOCUMENTS

WO    WO 01/42232 A1   6/2001

OTHER PUBLICATIONS

Gelin, Rene et al, Etude de la reaction de Prins entre des alcools β-ethyleniques et le formaldehyde, Comptes Rendus des Seances d l' Academie des Sciences, Serie C: Sciences Chimiques, 1972, vol. 275, No. 17, pp. 957-959.

Hanschke, E. et al, Zur Kenntnis der Prins schen Reaction, III. Mitteil.: Uber die Reaction von Allylcarbinol mit Aldehyden und Ketonen, Chem Ber., 1955, vol. 88, pp. 1053-1061.
Gerin, Rene et al, Etude de la reaction de Prins entre des alcohols β-ethyleniques et des aldehydes, Synthese de tetrahydropyrannols-4, Comptes Rendus des Seances de l'Academie des Sciences, Serie C: Sciences Chimiques, 1971, vol. 275, pp. 254-256.
Nishiura, Kazuo et al, The Reaction of Olefins with Chloroalkoxy-alkanes and Formic Acid in Ether, Bull. Chem. Soc. Jpn., 1980, vol. 53, pp. 1376-1380.
Fukui, Kenishi et al, Reaction of Propylene with Formaldehyde, Bull, Japan, Petrol. Inst., 1961, vol. 3, pp. 27-32.

*Primary Examiner*—Bernard Dentz
(74) *Attorney, Agent, or Firm*—Frishauf, Holtz, Goodman & Chick, P.C.

(57) ABSTRACT

The present invention relates to a process for preparing tetrahydropyran-4-ol which comprises the steps of (A) a cyclization step of preparing tetrahydropyranyl-4-formate represented by the formula (1):

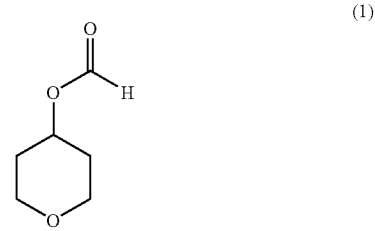

(1)

by reacting 3-buten-1-ol, a formaldehyde compound and formic acid, and
(B) then, a solvolysis step of subjecting the tetrahydropyranyl-4-formate to solvolysis to obtain tetrahydropyran-4-ol represented by the formula (2):

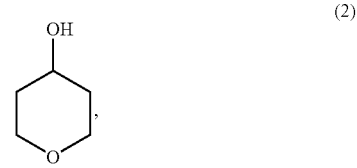

(2)

and an intermediate and a process for preparing the same.

21 Claims, No Drawings

PROCESS FOR PRODUCING TETRAHYDROPYRAN-4-OL, INTERMEDIATE THEREFOR, AND PROCESS FOR PRODUCING THE SAME

This application is the United States national phase application of International Application PCT/JP03/07357 filed Jun. 10, 2003.

TECHNICAL FIELD

The present invention relates to a novel process for preparing tetrahydropyran-4-ol and an intermediate thereof and a process for preparing the same. Tetrahydropyran-4-ol is a useful compound as a synthetic intermediate or starting material for a medicine, an agricultural chemical, etc.

BACKGROUND ART

In the prior art, as a process for preparing tetrahydropyran-4-ol, a method for producing tetrahydropyran-4-ol by reacting 3-buten-1-ol and formalin in the presence of a large amount of sulfuric acid with yield of 61% (based on 3-buten-1-ol) has been disclosed (Chem. Ber., 88, 1053 (1955)). This method involves, however, problems that yield is low, and a post-treatment of the sulfuric acid after completion of the reaction becomes complicated, or the like, and it was not advantageous as an industrial preparative process.

An object of the present invention is to solve the above-mentioned problems, and to provide an industrially preferred process for preparing tetrahydropyran-4-ol which requires no complicated post treatment, and can produce tetrahydropyran-4-ol with high yield.

SUMMARY OF THE INVENTION

The problem of the present invention can be solved by a process for preparing tetrahydropyran-4-ol which comprises:

(A) a cyclization step in which 3-buten-1-ol, a formaldehyde compound and formic acid are reacted to form a tetrahydropyranyl-4-formate represented by the formula (1):

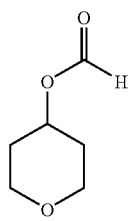

(1)

(B) then, a solvolysis step of subjecting the tetrahydropyranyl-4-formate to solvolysis to obtain tetrahydropyran-4-ol represented by the formula (2):

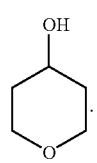

(2)

The problem of the present invention can be also solved by a process for preparing tetrahydropyranyl-4-formate represented by the formula (1):

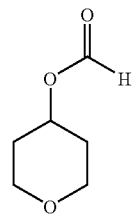

(1)

which comprises reacting tetrahydropyranyl-4-formate represented by the formula (1) with 3-buten-1-ol, a formaldehyde compound and formic acid to carry out the cyclization step.

BEST MODE FOR CARRYING OUT THE INVENTION

The present invention relates to a process for preparing tetrahydropyran-4-ol as a reaction product by the two steps of (A) a cyclization step of reacting 3-buten-1-ol, a formaldehyde compound and formic acid to obtain tetrahydropyranyl-4-formate represented by the formula (1), (B) then, a solvolysis step of subjecting tetrahydropyranyl-4-formate to solvolysis to form tetrahydropyran-4-ol represented by the formula (2).

Subsequently, the above-mentioned two steps are successively explained.

(A) Cyclization Step

The cyclization step of the present invention is a step of reacting 3-buten-1-ol, a formaldehyde compound and formic acid to prepare tetrahydropyranyl-4-formate.

The 3-buten-1-ol used as a starting material in the cyclization step of the present invention is a compound which can be easily synthesized by dehydration reaction of 1,4-butanediol (for example, Bull. Chem. Soc. Jpn., 54, 1585 (1981)) or monoepoxidization reaction of butadiene and subsequent reduction (for example, WO 9936379).

The formaldehyde compound to be used in the cyclization step of the present invention may be mentioned an aqueous solution of formaldehyde or a polymer of formaldehyde and the like, and at least one selected from the group consisting of, for example, formalin, paraformaldehyde and trioxane is suitably used.

An amount of the above-mentioned formaldehyde compound to be used is preferably 1.0 to 5.0 mol, more preferably 1.1 to 2.0 mol in terms of the formaldehyde based on 1 mol of 3-buten-1-ol used as a starting material. These formaldehyde compounds may be used alone or in combination of two or more kinds in admixture.

An amount of the formic acid (or it may be an aqueous solution thereof) to be used in the cyclization step of the present invention is preferably 1 to 20 mol, more preferably 2 to 10 mol based on 1 mol of 3-buten-1-ol as a starting material.

The cyclization step of the present invention can be carried out in the presence or absence of a solvent other than the formic acid. As the solvent to be used, it is not particularly limited so long as it does not inhibit the reaction, and it may be mentioned, for example, aromatic hydrocarbons such as benzene, toluene, xylene, mesitylene, etc.; halogenated hydrocarbons such as chloroform, dichloroethane, etc.; organic esters such as ethyl acetate, butyl acetate, etc.; ethers such as diethyl ether, tetrahydrofuran, diisopropyl ether, etc.

An amount of the above-mentioned solvent to be used is preferably 0 to 50 ml, more preferably 0 to 10 ml based on 1 g of 3-buten-1-ol. These solvents may be used alone or in combination of two or more kinds in admixture.

The cyclization step of the present invention can be carried out by, for example, mixing 3-buten-1-ol, a formaldehyde compound and formic acid under an inert gas atmosphere, and reacting them under stirring, and the like. The reaction temperature at that time is preferably 10 to 110° C., more preferably 50 to 100° C., and the reaction pressure is not specifically limited.

In the cyclization step of the present invention, a solution containing tetrahydropyranyl-4-formate as a main product can be obtained, and in the present invention, the next step is generally carried out by using the solution as such or after concentration. However, in some cases, the formed tetrahydropyranyl-4-formate may be once separated and purified by, for example, a general method such as crystallization, recrystallization, distillation, column chromatography, etc., and then, the next step may be carried out.

(B) Solvolysis Step

The solvolysis step of the present invention is a step of subjecting tetrahydropyranyl-4-formate to solvolysis to obtain tetrahydropyran-4-ol.

The solvolysis step of the present invention is not specifically limited so long as it is a method in which a formate can be generally subjected to solvolysis, and it is preferably carried out in the presence of an acid or a base, in water, an alcohol, or a mixed solvent of water and an alcohol.

As the acid mentioned above, there may be mentioned, for example, organic sulfonic acids such as methanesulfonic acid, ethanesulfonic acid, benzenesulfonic acid, p-toluenesulfonic acid, etc.; inorganic sulfonic acids such as sulfuric acid, chlorosulfuric acid, etc.; hydrohalogenated acid such as hydrofluoric acid, hydrochloric acid, hydrobromic acid, hydroiodic acid, etc.; halogenated carboxylic acids such as chloroacetic acid, dichloroacetic acid, etc., preferably organic sulfonic acids, inorganic sulfonic acids, more preferably organic sulfonic acids are used. Incidentally, these acids may be used alone or in combination of two or more kinds in admixture.

An amount of the above-mentioned acid to be used is preferably 0.1 to 200 mg, more preferably 2 to 50 mg based on 1 g of tetrahydropyranyl-4-formate.

When a base is used, it is preferred that formic acid is removed by a suitable means such as distillation, etc., or formic acid is neutralized, and then, an amount necessary for promoting the solvolysis reaction is added to the reaction system, further preferably it is an amount of 1 equivalent or less based on the amount of the tetrahydropyranyl-4-formate. As such a base, it is not specifically limited so long as it is a base generally used in the solvolysis reaction, and, for example, an inorganic base such as an alkali metal hydroxide salt, an alkali metal carbonate, an alkali metal hydrogen carbonate, etc., an organic base such as a tertiary amine, etc.

In the present invention, it is preferably carry out the solvolysis step by adding an acid since the reaction can promote effectively with less amount.

As the above-mentioned alcohol, there may be mentioned, for example, methanol, ethanol, n-propyl alcohol, isopropyl alcohol, n-butyl alcohol, sec-butyl alcohol, t-butyl alcohol, pentyl alcohol, methoxy ethanol, ethoxy ethanol, ethylene glycol, triethylene glycol etc., preferably methanol, ethanol, n-propyl alcohol, isopropyl alcohol, more preferably methanol, ethanol, isopropyl alcohol are used. Incidentally, these alcohols may be used alone or in combination of two or more, and water may be contained without any problem.

An amount of the above-mentioned alcohol to be used is preferably 1 to 100 mol, more preferably 5 to 50 mol based on 1 mol of tetrahydropyranyl-4-formate.

The solvolysis step of the present invention can be carried out by a method in which, for example, under an atmosphere of an inert gas, tetrahydropyranyl-4-formate, alcohol and an acid or a base are mixed, and reacted while stirring, and the like. The reaction temperature at that time is preferably 20 to 120° C., more preferably 30 to 70° C., and the reaction pressure is not specifically limited.

Incidentally, the tetrahydropyran-4-ol which is the final product can be isolated and purified by, for example, after completion of the solvolysis step, a general method such as concentration, distillation, recrystallization, column chromatography, etc.

EXAMPLE

Next, the present invention is specifically explained by referring to Examples, but the scope of the present invention is not limited by these examples.

Example 1

Synthesis of tetrahydropyran-4-ol

In a glass flask having an inner volume of 2 liters and equipped with a stirring device, a thermometer, a dropping funnel and a Dean-Stark device was charged 600 ml of 98% by weight formic acid, and the mixture was heated to 80° C. Thereafter, a solution containing 300 g (4.16 mol) of 3-buten-1-ol and 149.9 g (1.66 mol) trioxane dissolved in 600 ml of 98% by weight formic acid was gradually added dropwise to the above mixture over 4.5 hours, and under nitrogen atmosphere, the mixture was subjected to cyclization reaction at the same temperature for 8 hours.

Then, after cooling the reaction mixture to room temperature, 5.4 g (56 mmol) of methanesulfonic acids and 600 ml of ethanol were added to the mixture, and the resulting mixture was heated up to 64° C. under normal pressure, whereby solvolysis was carried out while removing by-producing ethyl formate. Moreover, after this operation was repeated three times, the reaction mixture was distilled under reduced pressure (85 to 87° C., 173 Pa) to obtain 347 g of tetrahydropyran-4-ol (Isolation yield based on 3-buten-1-ol: 81.6%) as a colorless liquid with a purity of 99.2% (areal percentage according to gas chromatography).

Example 2

Synthesis of tetrahydropyran-4-ol

In a glass flask having an inner volume of 500 ml and equipped with a stirring device, a thermometer, a dropping funnel and a Dean-Stark device were charged 27.0 g (374 mmol) of 3-buten-1-ol, 13.5 g (150 mmol) of trioxane and 133 ml of 98% by weight formic acid, and the mixture was subjected to cyclization under nitrogen atmosphere at 80° C. for 4 hours.

Then, formic acid was distilled off from the reaction mixture under reduced pressure, 1 g (10 mmol) of methanesulfonic acid and 200 ml of methanol were added to the residue, and the resulting mixture was heated up to 64° C. under normal pressure, whereby solvolysis was carried out while removing by-producing methyl formate. Moreover, after this operation was repeated, when the reaction mixture was analyzed by gas chromatography (internal standard method), 30.2 g of tetrahydropyran-4-ol was found to be formed (Reaction yield based on 3-buten-1-ol: 79%).

Example 3

Synthesis of tetrahydropyran-4-ol

The same reaction as in Example 2 was carried out except for changing methanol to ethanol in Example 2. As a result, 30.9 g of tetrahydropyran-4-ol was found to be formed (Reaction yield based on 3-buten-1-ol: 81%).

Example 4

Synthesis of tetrahydropyran-4-ol

The same reaction as in Example 2 was carried out except for changing methanol to isopropylalcohol in Example 2. As a result, 32.1 g of tetrahydropyran-4-ol was found to be formed (Reaction yield based on 3-buten-1-ol: 84%).

Example 5

Synthesis of tetrahydropyran-4-ol

In a glass flask having an inner volume of 500 ml and equipped with a stirring device, a thermometer, a dropping funnel and a Dean-Stark device were charged 10.0 g (139 mmol) of 3-buten-1-ol, 5.0 g (56 mmol) of trioxane and 40 ml of 98% by weight formic acid, the mixture was subjected to cyclization reaction under nitrogen atmosphere at 80° C. for 4 hours.

Then, 0.2 g (2 mmol) of methanesulfonic acid and 50 ml of ethanol were added to the mixture and the resulting mixture was heated up to 64° C., whereby solvolysis was carried out while removing by-producing ethyl formate. Moreover, after the operation was repeated, when the reaction mixture was analyzed by gas chromatography (internal standard method), 13.1 g of tetrahydropyran-4-ol was found to be formed (Reaction yield based on 3-buten-1-ol: 92%).

Example 6

Synthesis of tetrahydropyranyl-4-formate

In a glass flask having an inner volume of 1 liter and equipped with a stirring device, a thermometer and a Dean-Stark device were charged 100 g (1.39 mol) of 3-buten-1-ol, 50.0 g (0.56 mol) of trioxane and 500 ml of 98% by weight formic acid, and cyclization reaction was carried out under nitrogen atmosphere, at 80° C. for 8 hours. After completion of the reaction, it was concentrated under reduced pressure, and distilled under reduced pressure (92 to 94° C., 667 Pa) to obtain 131.6 g (Isolation yield based on 3-buten-1-ol: 69%) of tetrahydropyranyl-4-formate as a colorless liquid with a purity of 94.9% (areal percentage according to gas chromatography).

The tetrahydropyranyl-4-formate is a novel compound represented by the following physical properties. CI-MS (m/e); 131 (M+1) $^1$H-NMR (CDCl$_3$, δ (ppm)); 1.67 to 1.78 (2H, m), 1.91 to 2.00 (2H, m), 3.52 to 3.60 (2H, m), 3.90 to 3.97 (2H, m), 5.06 to 5.14 (1H, m), 8.60 (1H, s)

Example 7

Synthesis of tetrahydropyranyl-4-formate

In a glass flask having an inner volume of 25 ml and equipped with a stirring device and a thermometer were charged 1.00 g (13.9 mmol) of 3-buten-1-ol, 0.54 g (16.7 mmol) of 92% by weight paraformaldehyde and 5 ml of 98% by weight formic acid, and cyclization reaction was carried out under nitrogen atmosphere, at 80° C. for 4 hours. After completion of the reaction, when the reaction mixture was analyzed by gas chromatography (internal standard method), 1.77 g of tetrahydropyranyl-4-formate was found to be formed (Reaction yield based on 3-buten-1-ol: 98%).

Example 8

Synthesis of tetrahydropyranyl-4-formate

In a glass flask having an inner volume of 25 ml and equipped with a stirring device and a thermometer were charged 1.00 g (13.9 mmol) of 3-buten-1-ol, 0.50 g (5.6 mmol) of trioxane and 5 ml of 98% by weight formic acid, and cyclization reaction was carried out under nitrogen atmosphere, at 80° C. for 4 hours. After completion of the reaction, when the reaction mixture was analyzed by gas chromatography (internal standard method), 1.81 g of tetrahydropyranyl-4-formate was found to be formed (Reaction yield based on 3-buten-1-ol: 100%).

Example 9

Synthesis of tetrahydropyranyl-4-formate

In a glass flask having an inner volume of 25 ml and equipped with a stirring device and a thermometer were charged 1.00 g (13.9 mmol) of 3-buten-1-ol, 1.35 g (16.7 mmol) of 37% by weight aqueous formalin solution and 5 ml of 98% by weight formic acid, and cyclization reaction was carried out under nitrogen atmosphere, at 55° C. for 8 hours. After completion of the reaction, when the reaction mixture was analyzed by gas chromatography (internal standard method), 1.10 g of tetrahydropyranyl-4-formate was found to be formed (Reaction yield based on 3-buten-1-ol: 61%).

Example 10

Synthesis of tetrahydropyranyl-4-formate

In a glass flask having an inner volume of 25 ml and equipped with a stirring device and a thermometer were charged 1.00 g (13.9 mmol) of 3-buten-1-ol, 0.50 g (5.6 mmol) of trioxane and 5 ml of 98% by weight formic acid, and cyclization reaction was carried out under nitrogen atmosphere, at 120° C. for 8 hours. After completion of the reaction, when the reaction mixture was analyzed by gas chromatography (internal standard method), 1.47 g of tetrahydropyranyl-4-formate was found to be formed (Reaction yield based on 3-buten-1-ol: 81%).

Example 11

Synthesis of tetrahydropyranyl-4-formate

In a glass flask having an inner volume of 25 ml and equipped with a stirring device and a thermometer were charged 10.0 g (139 mmol) of 3-buten-1-ol, 5.0 g (56 mmol) of trioxane and 50 ml of 98% by weight formic acid, and cyclization reaction was carried out under nitrogen atmosphere, at 80° C. for 4 hours. After completion of the reaction, when the reaction mixture was analyzed by gas chromatography (internal standard method), 18.1 g of tetrahydropyranyl-4-formate was found to be formed (Reaction yield based on 3-buten-1-ol: 100%).

Example 12

Synthesis of tetrahydropyranyl-4-formate

In a glass flask having an inner volume of 25 ml and equipped with a stirring device and a thermometer were charged 2.0 g (28 mmol) of 3-buten-1-ol, 1.0 g (11 mmol) of trioxane, 6 ml of 98% by weight formic acid and 6 ml of toluene, and cyclization reaction was carried out under nitrogen atmosphere, at 80° C. for 8 hours. After completion of the reaction, when the reaction mixture was analyzed by gas chromatography (internal standard method), 2.9 g of tetrahydropyranyl-4-formate was found to be formed (Reaction yield based on 3-buten-1-ol: 81%).

UTILIZABILITY IN INDUSTRY

According to the present invention, a process for preparing tetrahydropyran-4-ol which requires no complicated post treatment, can produce tetrahydropyran-4-ol with high yield, and industrially suitable can be provided.

The invention claimed is:

1. A process for preparing tetrahydropyran-4-ol which comprises the steps of:
   (A) a cyclization step of preparing tetrahydropyranyl-4-formate represented by the formula (1):

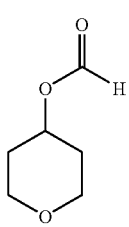

(1)

by reacting 3-buten-1-ol, a formaldehyde compound and formic acid, and
   (B) then, a solvolysis step of subjecting the tetrahydropyranyl-4-formate to solvolysis to obtain tetrahydropyran-4-ol represented by the formula (2):

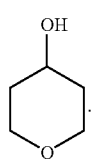

(2)

2. The process for preparing tetrahydropyran-4-ol according to claim 1, wherein the formaldehyde compound is at least one selected from the group consisting of formalin, paraformaldehyde and trioxane.

3. The process for preparing tetrahydropyran-4-ol according to claim 1, wherein the cyclization step is carried out by reacting 1.0 to 5.0 mol of the formaldehyde compound in terms of the formaldehyde and 1 to 20 mol of formic acid based on 1 mol of 3-buten-1-ol.

4. The process for preparing tetrahydropyran-4-ol according to claim 1, wherein the cyclization step is carried out by reacting 1.1 to 2.0 mol of the formaldehyde compound in terms of the formaldehyde and 2 to 10 mol of formic acid based on 1 mol of 3-buten-1-ol.

5. The process for preparing tetrahydropyran-4-ol according to claim 1, wherein the cyclization step is carried out in the presence or absence of a solvent at a temperature of 10 to 110° C.

6. The process for preparing tetrahydropyran-4-ol according to claim 1, wherein the cyclization step is carried out in the presence or absence of a solvent at a temperature of 50 to 100° C.

7. The process for preparing tetrahydropyran-4-ol according to claim 1, wherein the solvolysis step is carried out in the presence of an acid in water, alcohol, or a mixed solvent of water and an alcohol.

8. The process for preparing tetrahydropyran-4-ol according to claim 7, wherein the acid is at least one selected from the group consisting of organic sulfonic acids; inorganic sulfonic acids; hydrohalogeno acids; and halogenated carboxylic acids.

9. The process for preparing tetrahydropyran-4-ol according to claim 7, wherein the acid is at least one selected from the group consisting of methanesulfonic acid, ethanesulfonic acid, benzenesulfonic acid, p-toluenesulfonic acids, sulfuric acid, chlorosulfuric acid, hydrofluoric acid, hydrochloric acid, hydrobromic acid, hydroiodic acid, chloroacetic acid and dichloroacetic acid.

10. The process for preparing tetrahydropyran-4-ol according to claim 7, wherein the acid is used in an amount of 0.1 to 200 mg based on 1 g of the tetrahydropyranyl-4-formate.

11. The process for preparing tetrahydropyran-4-ol according to claim 7, wherein the alcohol is at least one selected from the group consisting of methanol, ethanol, n-propyl alcohol, isopropyl alcohol, n-butyl alcohol, sec-butyl alcohol, t-butyl alcohol, pentyl alcohol, methoxy ethanol, ethoxy ethanol, ethylene glycol and triethylene glycol.

12. The process for preparing tetrahydropyran-4-ol according to claim 7, wherein the alcohol is at least one selected from the group consisting of methanol, ethanol, n-propyl alcohol and isopropyl alcohol.

13. The process for preparing tetrahydropyran-4-ol according to claim 7, wherein the alcohol is used in an amount of 1 to 100 mol based on 1 mol of the tetrahydropyranyl-4-formate.

14. The process for preparing tetrahydropyran-4-ol according to claim 7, wherein the solvolysis step is carried out at a temperature of 20 to 120° C. and under stirring.

15. Tetrahydropyranyl-4-formate represented by the formula (1):

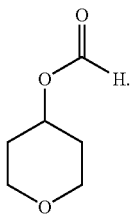

(1)

16. A process for preparing tetrahydropyranyl-4-formate represented by the formula (1)

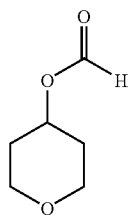

(1)

which comprises reacting 3-buten1-ol, a formaldehyde compound and formic acid.

17. The process for preparing tetrahydropyranyl-4-formate according to claim 16, wherein the formaldehyde compound is at least one selected from the group consisting of formalin, paraformaldehyde and trioxane.

18. The process for preparing tetrahydropyranyl-4-formate according to claim 16, wherein the reaction is carried out by reacting 1.0 to 5.0 mol of the formaldehyde compound in terms of the formaldehyde and 1 to 20 mol of formic acid based on 1 mol of 3-buten-1-ol.

19. The process for preparing tetrahydropyranyl-4-formate according to claim 16, wherein the reaction is carried out by reacting 1.1 to 2.0 mol of the formaldehyde compound in terms of the formaldehyde and 2 to 10 mol of formic acid based on 1 mol of 3-buten-1-ol.

20. The process for preparing tetrahydropyranyl-4-formate according to claim 16, wherein the reaction is carried out in the presence or absence of a solvent at a temperature of 10 to 110° C.

21. The process for preparing tetrahydropyranyl-4-formate according to claim 16, wherein the reaction is carried out in the presence or absence of a solvent at a temperature of 50 to 100° C.

* * * * *